(12) United States Patent
Miller

(10) Patent No.: US 8,246,698 B2
(45) Date of Patent: Aug. 21, 2012

(54) DYES WITH CHANGEABLE SOLUBILITIES, AND METHODS FOR THEIR USE

(75) Inventor: Seth Adrian Miller, Englewood, CO (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/126,132

(22) PCT Filed: Dec. 22, 2010

(86) PCT No.: PCT/US2010/061803
§ 371 (c)(1),
(2), (4) Date: Apr. 26, 2011

(65) Prior Publication Data
US 2012/0164288 A1 Jun. 28, 2012

(51) Int. Cl.
*C09B 67/00* (2006.01)
*C07D 253/00* (2006.01)
(52) U.S. Cl. .......... 8/565; 8/566; 8/587; 8/588; 544/183
(58) Field of Classification Search .............. 8/565, 566, 8/587, 588; 544/183
See application file for complete search history.

(56) References Cited

U.S. PATENT DOCUMENTS

| | | | |
|---|---|---|---|
| 3,942,987 A | 3/1976 | Landholm et al. | |
| 4,559,290 A | 12/1985 | Sawada et al. | |
| 5,998,588 A | 12/1999 | Hoffman et al. | |
| 6,200,963 B1 * | 3/2001 | Wrobel et al. | 514/150 |
| 7,625,764 B2 | 12/2009 | Stayton et al. | |
| 2008/0220531 A1 | 9/2008 | Stayton et al. | |

FOREIGN PATENT DOCUMENTS

WO WO-88/07568 10/1988

OTHER PUBLICATIONS

STIC Search Report dated Apr. 20, 2012.*
Baran, P.S., et. al, "Total Synthesis of Marine Natural Products Without Using Protecting Groups," Nature, Mar. 22, 2007, vol. 446, pp. 404-408.
Bochet, C. G., "Photolabile protecting groups and linkers," J. Chem. Soc., Perkin Trans. 1, 2002, pp. 125-142.
CAS RN 754974-11-3., STN Entry Date: Oct. 1, 2004, 1 page.
Hagemann, O. et al., "All solution processed tandem polymer solar cells based on thermocleavable materials," Sol. Energy Mater. Sol. Cells, 2008, vol. 92, pp. 1327-1335.
International Search Report and Written Opinion received for PCT/US2010/061803 mailed Feb. 16, 2011, 11 pages.
Jorgensen, et al., "Thermo-cleavable solvents for printing conjugated polymers: Application in polymer solar cells," Solar Energy Materials & Solar Cells, 2009, vol. 93, pp. 413-421.
Lewis, D. M., et al., "The Synthesis and Application of a New Reactive Dye Based on Disulfide-bis-ethylsulfone," Dyes and Pigments, 2000, vol. 47, pp. 151-167.
Pandey, A., et al. "Bacterial Decolorization and Degradation of Azo Dyes," International Biodeterioration & Biodegradation, 2007, vol. 59, pp. 73-84.
Suwanruji, P., "The Design, Synthesis and Application of Easy Wash Off Reactive Dyes," Dissertation, Fiber and Polymer Science, Aug. 2, 2004, retrieved from the internet: <URL: http://repository.lib.ncsu.edu/ir/bitstream/1840.16/4342/1/etd.pdf>, 150 pages.
Suzuki, A. Z. et al.,"Coumarin-4-ylmethoxycarbonyls as Phototriggers for Alcohols and Phenols," Organic Letters, 2003, vol. 5, No. 25, pp. 4867-4870.
Zielinska, B. et al., "Photocatalytic decomposition of textile dyes on $TiO_2$-Tytanpol A11 and $TiO_2$-Degussa P25," *Journal of Photochemistry and Photobiology A: Chemistry*, 2003, vol. 157, pp. 65-70.

* cited by examiner

*Primary Examiner* — Eisa Elhilo
(74) *Attorney, Agent, or Firm* — Foley & Lardner LLP

(57) ABSTRACT

Disclosed herein are solubility changeable dye compositions, methods of preparing such compositions and methods of using them. The composition includes a dye component linked via a linker moiety to a stimulus responsive hydrophobic moiety which modulates the solubility of the dye, wherein the hydrophobic moiety is configured to be de-linked from the dye component on exposure to a stimulus and render the dye component more hydrophilic.

16 Claims, No Drawings

DYES WITH CHANGEABLE SOLUBILITIES, AND METHODS FOR THEIR USE

CROSS-REFERENCE TO RELATED APPLICATIONS

The present application is a U.S. national stage application claiming the benefit of International Application No. PCT/US2010/061803, filed on Dec. 22, 2010, the entire contents of which is incorporated herein by reference in its entirety.

TECHNOLOGY

The present technology is related in general to dyestuffs. In particular, the present technology relates to the field of solubility changeable dyes.

BACKGROUND

The following description is provided to assist the understanding of the reader. None of the information provided or references cited is admitted to be prior art to the present technology.

New and improved dyes are being used for a wide variety of applications in dyeing and printing industries, textile industries, paper and ink manufacturing industries, cosmetics, and food and pharmaceutical industries. Textile dyes or fabric dyes consume nearly two thirds of the total dyes manufactured. Lately, the demand for reactive dyes has increased owing to their bright colors and improved stability. Reactive dyes bind to the substrate by addition or substitution mechanisms under alkaline conditions and high temperature, usually conducted as a batch process. During the batch dying process, a significant fraction of the dye is hydrolyzed and released. Moreover, at the end of the dying process, excess dye is rinsed off using large quantities of water, usually in a multistep process, at boiling temperatures. Consequently, both dye manufacturing and dye consuming industries produce wastewater which is highly colored, containing excess dye, high levels of electrolytes, toxic substances (e.g., metals and unreacted raw materials) and auxiliaries. This wastewater has high pH and poses unacceptable environmental risks and severe effluent treatment problems.

Ideally, fixation of the dye to the substrate is 100% efficient, that is every molecule of dye supplied to the substrate is fixed so that none appears in a waste stream. It is desirable: 1) to achieve a fixation rate as high as possible, using a minimum of associated chemicals and water; and 2) to efficiently remove excess dye, using a minimum of associated chemicals and water.

One of the most popular approaches for dyeing is to use a reactive dye, where a covalent bond between a substrate and a dye is created when the system pH is raised. For perfect fixation at this high pH, reactive groups on the substrate surface must outcompete water for these reactive sites on the dye. Dye molecules that react with water are inactivated and are no longer able to bond covalently with the substrate and must be rinsed away. As a result, dyes are commonly designed to be hydrophobic to increase their tendency to associate with the substrate (compared with water) and to slow the overall kinetics of reaction with water. However, perfection is not attainable and a fraction of the dye will usually hydrolyze rather than react with the substrate surface and must be rinsed away. Under these conditions, the dye's hydrophobicity turns from an asset to a liability because hydrophobic dyes require a large amount of water to be rinsed off completely.

The optimization of a typical dye application process takes into account several opposing parameters, especially related to waste disposal, which can significantly impact the total process cost. For example, during the dyeing process, a more hydrophobic molecule is preferred, as this will cause it to associate with the substrate rather than with water and, therefore, improve fixation efficiency and reduce overall wastes. However, an increase in the dye fixation as a result of increased hydrophobicity is often accompanied by the drawback of requiring much larger water volumes to remove unfixed dye after treatment. Current solutions must find a compromise between dye performance and its ease of removal and, therefore, fail to optimize either attribute.

SUMMARY

The present technology provides a reactive dye which is modified with a hydrophobic substituent that can subsequently be removed with the application of an external stimulus. After treating a substrate with the reactive dye, the stimulus is applied and the dye is rendered more hydrophilic. Because the water solubility of the dye is improved, any excess dye which remains unfixed on the substrate can be washed off using minimal water. The resulting process will reduce or minimize water use in both dye application and dye removal.

In one aspect, a dye compound is provided including a hydrophilic dye moiety; and a hydrophobic moiety bonded to the hydrophilic dye moiety through a linker moiety; where the linker moiety is cleaved in response to a stimulus. In some embodiments, the stimulus is provided by photolysis, thermolysis, enzymes or chemicals. In other embodiments, the dye moiety is a moiety of a fabric dye or an ink dye.

In another aspect, a method for modulating the solubility of a dye compound is provided, the method including exposing a dye composition to a stimulus, where the dye composition includes a plurality of the dye compounds, each dye compound including a hydrophilic dye moiety; and a hydrophobic moiety bonded to the hydrophilic dye moiety through a linker moiety; and the linker moiety is cleaved in response to the stimulus. In some embodiments, the method also includes contacting a substrate and the dye composition for a time period sufficient to covalently bond at least a portion of the plurality of the dye compounds to the substrate, prior to exposing.

In another aspect, a dye composition is provided including a dye moiety linked via a linker moiety to a stimulus responsive hydrophobic moiety which modulates the solubility of the dye, wherein the hydrophobic moiety is configured to be de-linked from the dye component on exposure to a stimulus and increase the dye component's hydrophilicity.

DETAILED DESCRIPTION

In the description that follows, a number of terms are used extensively. Definitions are provided to facilitate understanding of the technology. The terms described below are more fully defined by reference to the specification as a whole. Units, prefixes, and symbols may be denoted in their accepted SI form.

The terms "a" and "an," as used herein, mean "one or more" unless the singular is expressly specified. Thus, for example, reference to "a dye" includes a mixture of two or more such compounds, as well as a single compound.

Generally, reference to a certain element such as hydrogen or H is meant to include all isotopes of that element. For example, if an R group is defined to include hydrogen or H, it also includes deuterium and tritium. Compounds including radioisotopes such as tritium, $C^{14}$, $P^{32}$ and $S^{35}$ are thus within the scope of the technology. Procedures for inserting such labels into the compounds of the technology will be readily apparent to those skilled in the art based on the disclosure herein.

Various groups described herein may include both substituted or unsubstituted groups. In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having the number of carbons indicated herein. In some embodiments, an alkyl group has from 1 to 12 carbon atoms, 1 to 10 carbon atoms, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. In some embodiments, representative substituted alkyl groups may be substituted one or more times with substituents such as those listed above and include, without limitation, haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments, the number of ring carbon atoms range from 3 to 5, 3 to 6, or 3 to 7. Bi- and tricyclic ring systems include both bridged cycloalkyl groups and fused rings such as, but not limited to, bicyclo[2.1.1]hexane, adamantyl, decalinyl, and the like. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once such as, but not limited to, 2,2-, 2,3-, 2,4- 2,5- or 2,6-disubstituted cyclohexyl groups, which may be substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, naphthyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems such as, for example, imidazolyl, imidazolinyl and imidazolidinyl groups. The phrase "heterocyclyl group" includes fused ring species including those including fused aromatic and non-aromatic groups such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups such as alkyl, oxo or halo groups, bonded to one of the ring members. Rather, these are referred to as "substituted heterocyclyl groups." Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once such as, but not limited to, pyridyl or morpholinyl groups, which are 2-, 3-, 4-, 5-, or 6-substituted, or disubstituted with various substituents such as those listed above.

Groups described herein having two or more points of attachment (i.e., divalent, trivalent, or polyvalent) within the compound of the technology are designated by use of the suffix, "ene." For example, divalent alkyl groups are alkylene groups, divalent aryl groups are arylene groups, divalent heteroaryl groups are heteroarylene groups, and so forth. Substituted groups having a single point of attachment to the compound of the technology are not referred to using the "ene" designation. Thus, for example, chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include, but are not limited to, methoxy, ethoxy, propoxy, butoxy, pentoxy, hexoxy, and the like. Examples of branched alkoxy groups include, but are not limited to, isopropoxy, sec-butoxy, tert-butoxy, isopentoxy, isohexoxy, and the like. Examples of cycloalkoxy groups include, but are not limited to, cyclopropyloxy, cyclobutyloxy, cyclopentyloxy, cyclohexyloxy, and the like. Representative substituted alkoxy groups may be substituted one or more times with substituents such as those listed above.

The term "amine" (or "amino"), as used herein, refers to —$NR^{35}R^{36}$ groups, wherein $R^{35}$ and $R^{36}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is $NH_2$, methylamino, dimethylamino, ethylamino, diethylamino, propylamino, isopropylamino, phenylamino, or benzylamino. The term "alkylamino" is defined as —$NR^{37}R^{38}$, wherein at least one of $R^{37}$ and $R^{38}$ is alkyl and the other is alkyl or hydrogen. The term "arylamino" is defined as —$NR^{39}R^{40}$, wherein at least one of $R^{39}$ and $R^{40}$ is aryl and the other is aryl or hydrogen.

The term "hydroxy" or "hydroxyl," as used herein, can refer to —OH or its ionized form, —$O^-$.

As used herein, the phrase "alkali metal" refers to an element in Group 1 (International Union of Pure and Applied Chemistry (IUPAC)) of the periodic table of the chemical elements, and includes, e.g., cesium (Cs), francium (Fr), lithium (Li), potassium (K), rubidium (Rb) and sodium (Na).

The term "dye," as used herein, can generally be described as a colored substance that has an affinity for the substrate to which it is being applied.

As used herein, the term "hydrophilic" means that the compound has an affinity for water, whereas "hydrophobic" means not having an affinity for water. The terms are relative terms, where a hydrophilic compound it has a higher affinity for water than a hydrophobic compound, but the hydrophilic compound may or may not be completely water soluble. Likewise, hydrophobic materials have less of an affinity for water than hydrophilic materials, but the hydrophobic materials may not necessarily be water-repellant. While hydrophilic materials have an affinity for water and other polar solvents, hydrophobic materials tend to have an affinity for oils, fats, and other non-polar solvents.

In one aspect, the present technology provides a dye compound that includes a hydrophilic dye moiety bound to a hydrophobic moiety through a linker group. The hydrophobic moiety has sufficient hydrophobic character to render the dye compound overall hydrophobic. The hydrophilic dye moiety may be covalently to a substrate. Thus, when a solution of the dye compound is exposed to the substrate, at least some of the hydrophilic dye moieties covalently bind to the substrate. However, once the substrate is dyed by contacting a solution of the dye compound to the substrate, it is exposed to a stimulus the linker is cleaved, thereby separating the hydrophobic moiety from the hydrophilic dye moiety. When this occurs, the dye moiety that is bound to the substrate remains with the substrate, however any excess dye moiety that is unbound may then be readily washed away with an aqueous wash to easily remove the excess dye.

Typically, the substituent upon activation by a stimulus will increase the hydrophilicity of the dye compound as described above, although the reverse is also envisioned. In some cases, the increase will change the dye compound from hydrophobic to hydrophilic, but in other cases the increase will be from more hydrophobic to less hydrophobic. For example, where a hydrophilic dye moiety and a hydrophobic moiety are described, it is envisioned that it may be hydrophobic dye moiety and a hydrophilic moiety may be used in the alternative, with the opposite result. For example, where if the dye compound contains a hydrophobic dye moiety linked to a hydrophilic moiety, and the dye compound is exposed to a stimulus after covalently bonding at least some of the hydrophobic dye moieties to a substrate, the excess dye may then be removed with successive non-aqueous washes in which the hydrophobic dye moiety is soluble. Accordingly, disclosed herein are dyes which are capable of changing their solubility in response to a stimulus, compositions including such dyes, and methods of modulating the solubility of dyes.

In accordance with one aspect, a dye compound includes a hydrophilic dye moiety a hydrophobic moiety and optionally a linker moiety. The dye moiety is configured to be covalently bonded to a substrate. In some embodiments, the hydrophobic moiety is bonded to the dye moiety through a linker moiety, which is cleavable upon exposure to a stimulus. Thus, when the hydrophobic moiety is removed by cleavage of the linker, the hydrophilic dye may be removed with an aqueous wash. Generically, the dye compound can be represented by Dye-L-Z, where Dye is the dye moiety, L is the linker moiety, and Z is the hydrophobic moiety. Depending on the particular linking group used, a portion of the linking group may remain attached to the dye moiety after exposure to the stimulus.

The stimulus that may be applied to cleave the liner can include, but is not limited to, an electrical stimulus, a mechanical stimulus, a chemical stimulus, a thermal stimulus, or a light stimulus. For example, an electrical stimulus may include an electrical circuit that delivers electrical pulse or series of pulses which act on the linker to cleave or break, the link. A mechanical stimulus may include ultrasonic vibration or other physical action on the linker. A chemical stimulus may include a chemical reaction with the linker by any of a number of reactions including the use of enzymatic action. A thermal stimulus may include a heating element or cooling element. A light stimulus may include a light source such as a ultraviolet, infrared, visible or other light source. Thus, in some embodiments, the stimulus to cleave the linker moiety may be provided by using photolysis, thermolysis, enzymes or other chemicals using suitable stimulating devices. For example, photolysis can be employed to cleave photolabile groups such as O-nitrobenzyloxy, O-nitroveratryl or phenacyl groups, thermolysis or thermal decomposition may be used to cleave a carboxylic acid linkage, and an enzyme can be used to cleave a fatty acid linker.

The dye moiety may include any suitable dye known in the art capable of adhering to the substrate, ideally by forming a covalent bond, and which can be bonded to a hydrophobic moiety via a suitable linker moiety. In some embodiments, the dye moiety includes an aryl group with at least one substituent that is hydrophilic. Examples of such dye moieties may be derived from and include, but are not limited to, Procion Red MX-5B, Cibacron Brilliant Red 3B-A, Reactive Red 3, Cibacron Brilliant Yellow 3G, Reactive Blue 4, Reactive Blue 2, Reactive Orange 14, Reactive Orange 4, Procion MX-R, Remazol Orange-16, Reactive Green 19, C.I Reactive Red 221 and Reactive Red 120. The hydrophilic substituents on the dye moiety are well-known in the art and may include, but are not limited to, OH, C(O)OH, C(O)O($C_1$-$C_8$ alkyl), C(O)O($C_1$-$C_8$ cycloalkyl), SH, $NO_2$, $NH_2$, CN, $SO_3$, $OSO_3$, C(O)$NH_2$, and $PO_3$.

The hydrophobic moiety may include any suitable hydrophobic groups known in the art. In some embodiments, the hydrophobic moiety includes, but is not limited to, an alkyl group, a cycloalkyl group, or an aryl group. These groups may be substituted or unsubstituted. In some embodiments, the hydrophobic moiety is a short chain, medium chain or long chain hydrocarbon having from about two to about 22 carbon atoms. In other embodiments, the hydrophobic moiety may include phenyl groups, cycloalkanes, alkenes, silicones or fluorocarbons.

The hydrophobic moiety can be bonded to the dye moiety either directly or by using any suitable linker moiety or linking groups known in the art. The type of linker moiety used will depend on various factors such as the structure of the dye moiety, structure of the hydrophobic moiety and the type of stimulus to be applied. The linker moiety is typically chemically stable under the conditions of the actual application of the dye and does not interfere with the reaction of the dye with the substrate, but may be constructed such as to be cleaved at some point in time after the application or fixing of some of the dye to the substrate. A suitable linker moiety may include one or more simple groups such as, but not limited to, a direct bond, an ester, ether, amide, carbonyl, phosphate, sulfoxide or more complex groups such as, but not limited to, nitrophenyl, nitrobenzyl, alkoxybenzoin, phenacyl, or benzylthioether group. Examples of suitable linker moieties and the conditions under which they can be cleaved are described in, for example, *J. Chem. Soc., Perkin Trans.* 1, 2002, pp. 125-142.

The substrate may be any suitable material which can adhere to the dye moiety and, in some embodiments, is capable of forming a covalent bond with the dye moiety. Suitable substrates may include, but are not limited to, fabric, paper, plastics, glass, metals, wood, hair, fur, oils, waxes, leather or food. In an illustrative embodiment, the substrate is a fabric. In some embodiments, the substrate includes cellulosic material such as paper, paperboard, and textiles made from cotton, linen, and other plant fibers. For purposes of illustration, the examples described below relate to textile or fabric dyes. However, the technology would apply to a variety of substrates including all types of substrates described above.

Depending on the substrate, the dye moiety may be a fabric dye, an ink dye, a hair color, food color, etc. In some embodiments, the dye moiety is a fabric dye or an ink dye. Several categories and types of dyes are known in the art and can be used in the present technology. These include natural dyes, synthetic dyes, direct dyes, vat dyes, sulphur dyes, azo dyes and reactive dyes among other categories. In some embodiments, the dye moiety can be a reactive dye which is capable of undergoing stable covalent bond formation with the substrate. As an illustrative embodiment, reactive dyes having one or more chlorotriazine groups are suitable for use in the present compositions. In other embodiments, the reactive dye can be one which does not include a chlorotriazine group such as, e.g., Remazol Orange 16. Suitable dye moieties include, for example, those listed Klaus Hunger, *Industrial dyes: chemistry, properties, application*, Wiley-VCH, 2003.

In some embodiments, the dye compound is represented by Formula (I)

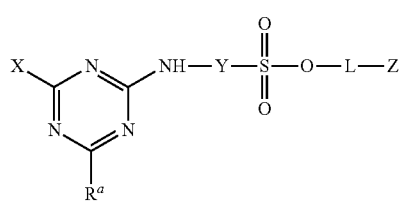

wherein Z is the hydrophobic moiety; L is the linker moiety; Y is a phenyl or a naphthyl group; X is selected from the group consisting of H, Cl, Br, F, and I; $R^a$ is a halogen, or —$NR^b$—W group; $R^b$ is H or an alkyl group; and W includes a phenyl, naphthyl or anthracenyl group.

In some embodiments, the dye compound is represented by Formula (II)

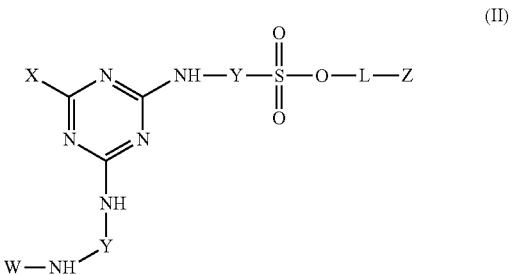

wherein Z is the hydrophobic moiety; L is the linker moiety; X is selected from the group consisting of H, Cl, Br, F, and I; each Y independently is a phenyl or a naphthyl group; and W includes a phenyl, naphthyl or anthracenyl group.

In some embodiments, the dye compound is represented by Formula (III)

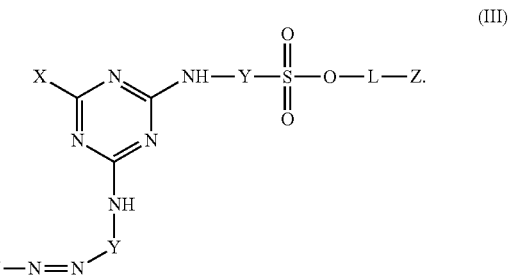

wherein Z is the hydrophobic moiety; L is the linker moiety; X is selected from the group consisting of H, Cl, Br, F, and I; each Y independently is a phenyl or a naphthyl group; and W includes a phenyl, naphthyl, anthracenyl or pyrazolinyl group.

In some embodiments, the dye compound is represented by Formula (IV)

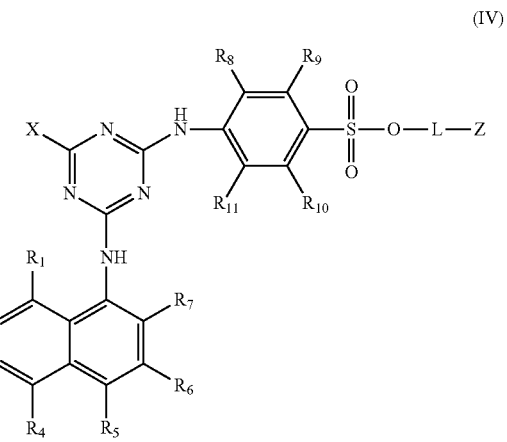

wherein Z is the hydrophobic moiety; L is the linker moiety; X is selected from the group consisting of H, Cl, Br, F, and I; $R_1$, $R_2$, $R_3$, $R_4$, $R_5$, $R_6$, and $R_7$ may be the same or different and are independently H, Cl, Br, F, I, $NO_2$, OH, alkyl, aryl, or $S(=O)_3R_{12}$; $R_8$, $R_9$, $R_{10}$, and $R_{11}$ may be the same or different and are independently H or alkyl; and $R_{12}$ is H or an alkali metal. In an illustrative embodiment, $R_{12}$ is H or Na.

In some embodiments, the dye compound includes an azo dye moiety. In some such embodiments, the dye compound is represented by Formula (V)

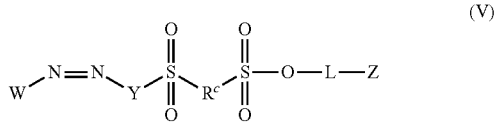

(V)

wherein Z is the hydrophobic moiety; L is the linker moiety; $R^c$ is an alkyl or alkoxy group; Y includes a phenyl or a naphthyl group; and W includes a phenyl, or naphthyl group.

The hydrophobic moiety Z and the linker moiety L in dye compounds of Formula (I)-(V) may be as defined herein. In some embodiments, the hydrophobic moiety Z includes an alkyl group, a cycloalkyl group, or an aryl group. In some embodiments, the linker moiety L includes a direct bond, an ester, ether, amide, carbonyl, phosphate, sulfoxide or more complex groups such as, but not limited to, nitrophenyl, nitrobenzyl, alkoxybenzoin, phenacyl, or benzylthioether group. In some embodiments, each Y is independently phenyl or naphthyl. In some embodiments, W includes an aryl group that is phenyl, naphthyl, anthracenyl or a heterocyclyl group such as, e.g., a pyrazolinyl group.

In some embodiments, each of the groups described in the above structures may optionally be substituted. For example, the phenyl, naphthyl or anthracenyl group may have one or more sulfonic acid groups, amino groups or hydroxyl groups. The anthracenyl group may be an anthroquinone which may optionally have substituents such as sulfonic acid group, hydroxyl group or an amino group. The pyrazolinyl group may be a pyrazolone which may optionally have substituents such as alkyl or substituted phenyl group. A few examples of reactive dye moieties having the structures that are representative of the compounds represented by Formulas (I)-(V) are given in Table 1 below.

TABLE 1

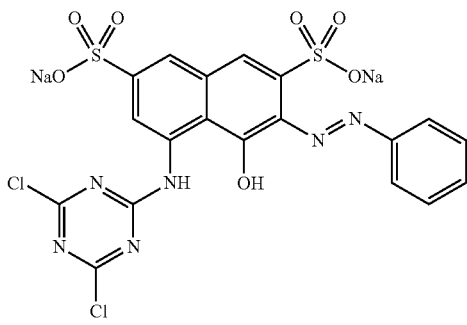

Procion Red MX-5B

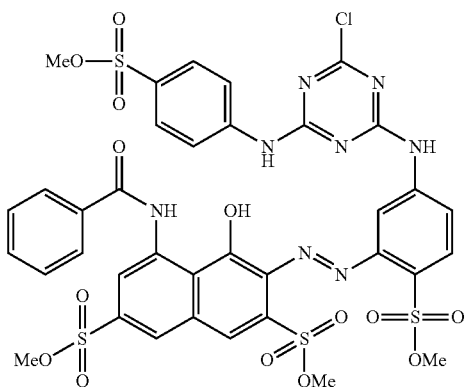

Cibacron Brilliant Red 3B-A

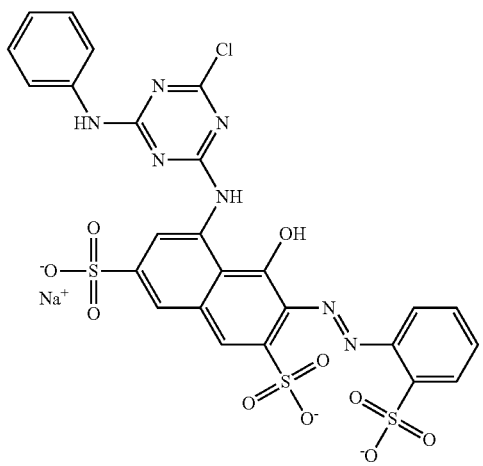

Reactive Red 3

TABLE 1-continued
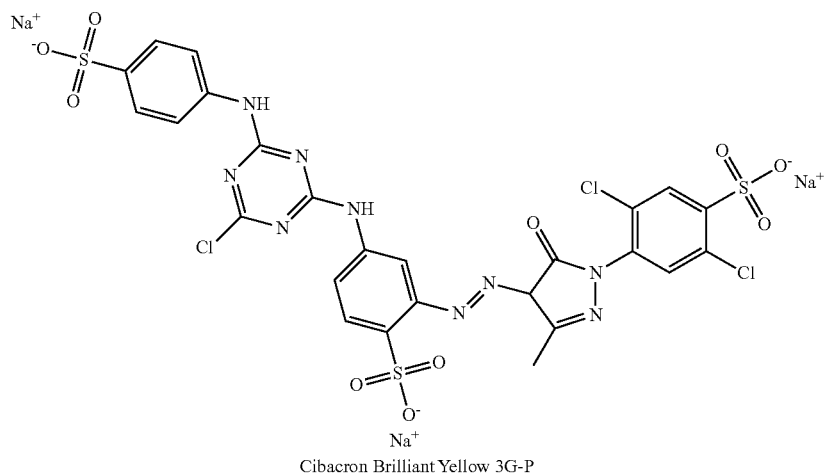
Cibacron Brilliant Yellow 3G-P
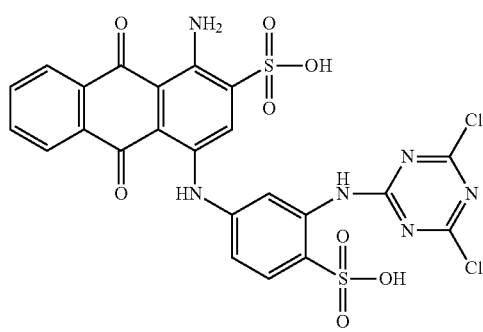
Reactive Blue 4
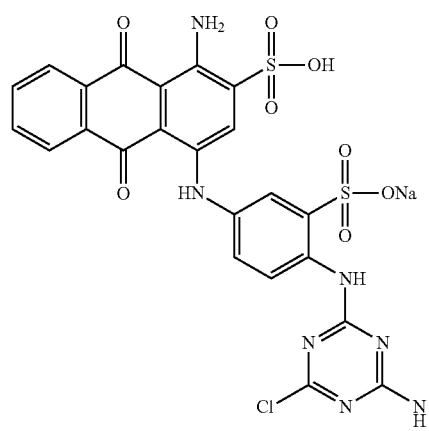
R = H or SO₃Na
(one of each)
Reactive Blue 2
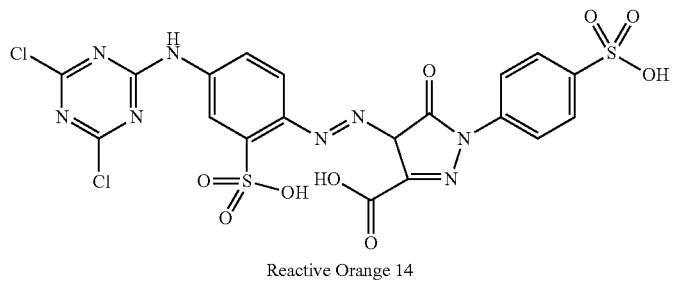
Reactive Orange 14
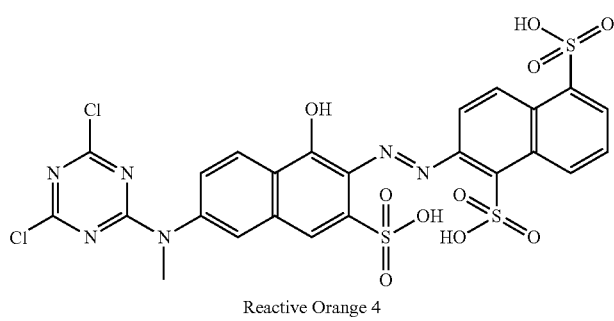
Reactive Orange 4

TABLE 1-continued

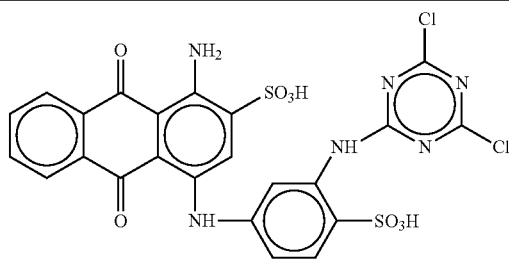

Procion MX-R

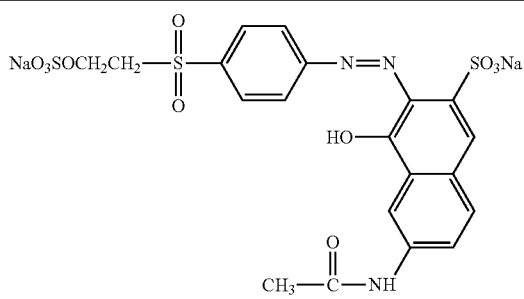

Remazol Orange-16

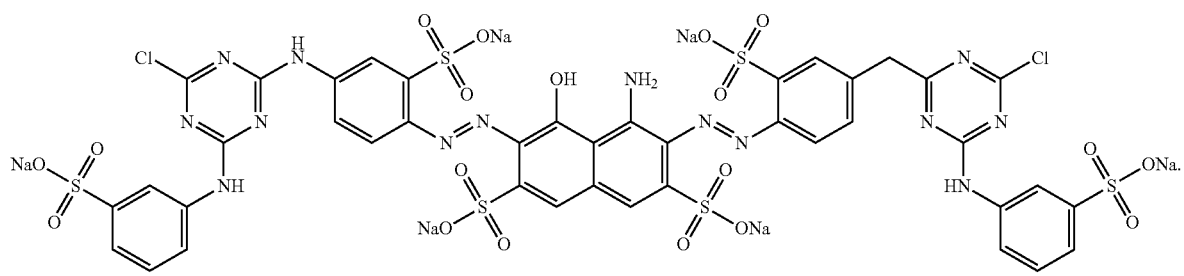

Reactive Green 19

The dye compound used in the present technology can be synthesized using commonly used chemical methods known in the art. For example, in one embodiment, a photolabile group can be added to the chlorotriazine ring of a reactive dye moiety as shown in the following synthetic Scheme 1. Photolabile groups include groups which are labile under photolytic conditions and can be removed by subjecting them to photophysical or photochemical reactions. Photolabile groups such as substituted 2-nitrobenzyls, 3-nitrophenyls, benzoins, and phenacyls, are known to those skilled in the art and can be added or removed using well-known procedures such as those set forth in *J. Chem. Soc., Perkin Trans.* 1, 2002, 125-142. The identity of the final product can be determined by a method such as NMR, mass spectrometry, and x-ray crystallography.

Scheme I

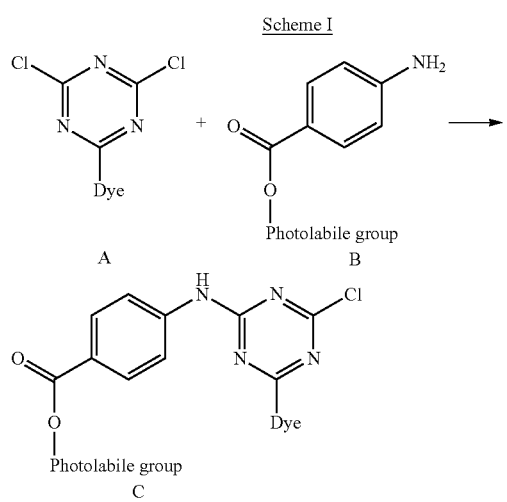

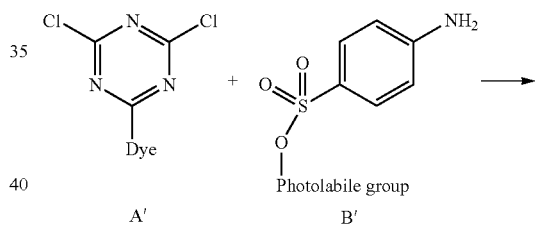

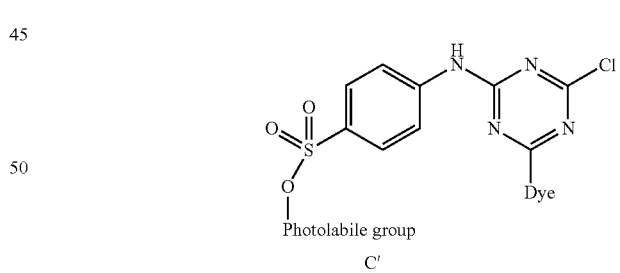

The chlorotriazine group of the dye moiety A can react with the free amine in the photolabile compound B and forms a hydrophobic conjugate C which can be applied to the substrate. Once the application process is complete, the dye solution can be photolyzed to remove the photolabile group creating a hydrophilic dye moiety D, shown in Scheme II, which can be easily washed away using decreased quantities of water.

Scheme II

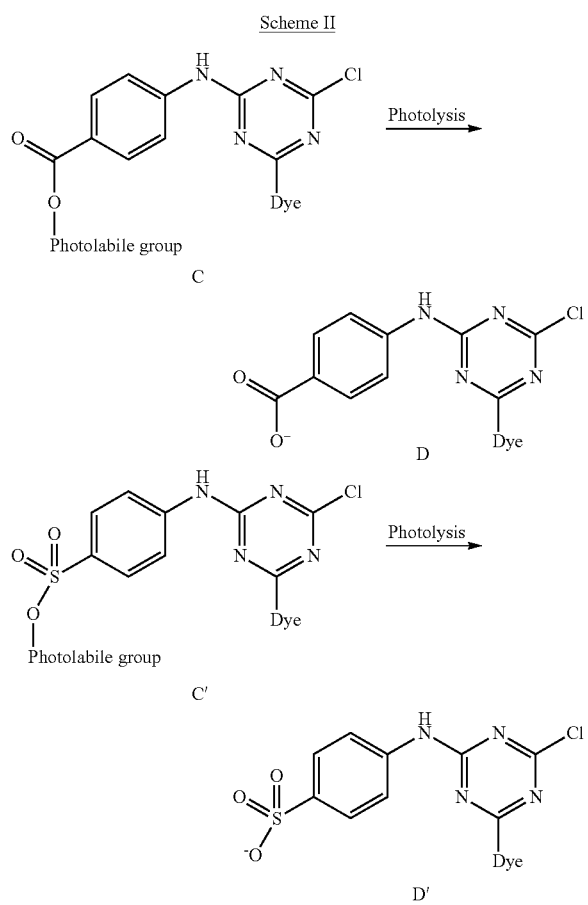

The dye moiety A in Schemes I and II can be, for example, Procion Red MX-5B, which has the following structure:

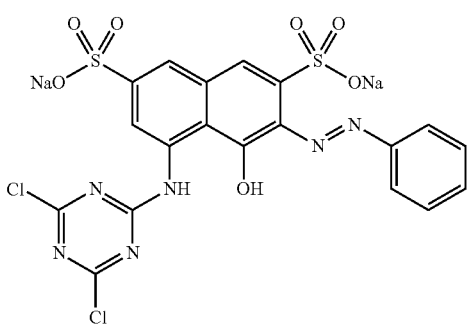

The photolabile component B in Schemes I and II can be prepared, for example, according to Scheme III below:

Scheme III

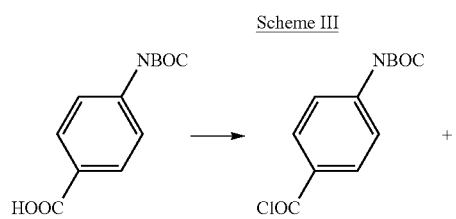

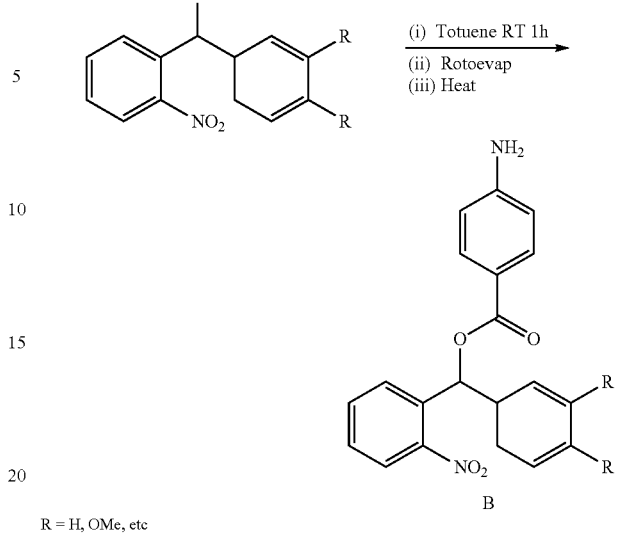

R = H, OMe, etc

In various aspects, the present technology provides a dye composition which includes a dye moiety linked via a linker moiety to a stimulus responsive hydrophobic moiety which modulates the solubility of the dye, where the hydrophobic moiety is configured to be de-linked from the dye component on exposure to a stimulus and render the dye component hydrophilic.

The compositions described above find application in a wide variety of industries including dyeing and printing industries, textile industries, paper and ink manufacturing industries, cosmetics, and food and pharmaceutical industries.

In another aspect, a method for modulating the solubility of a dye is provided. In one embodiment, the method includes exposing a dye composition to a stimulus, where the dye composition includes a dye compound. In some embodiments, the dye compound includes a dye moiety; and a hydrophobic moiety bonded to the dye moiety through a linker moiety. In some embodiments of the method, the dye moiety is configured to covalently bond to a substrate; and the linker moiety is configured to be cleaved in response to the stimulus to render the dye moiety hydrophilic.

In some embodiments, the method further includes contacting the substrate with the dye composition for a time period sufficient to covalently bond at least some the dye moieties to the substrate prior to exposing the dye composition to stimulus. In some embodiments, the method further includes washing the substrate to remove the hydrophilic dye moiety with water after exposing the dye composition to a stimulus. Where dye moieties are present in the composition which have not reacted with the substrate to covalently bind to the substrate, the application of the stimulus renders the dye moieties that are unbound more water soluble. Accordingly, these excess dyes may then be readily washed from the substrate with minimal waste water washing.

Suitable substrates may include those selected from the group consisting of fabric, paper, plastics, glass, metals, wood, hair, fur, oils, waxes, leather and food. In some embodiments of the method, the substrate is a fabric or a textile.

In some embodiments, the method includes applying the dye onto a substrate, fixing the dye at elevated pH, applying stimulus to change the dye's hydrophobicity (or hydrophilicity), and removal of excess hydrophilic dye.

In a commercial dying process, the substrate is typically soaked in an aqueous dye solution, the substrate is retained in the solution for a period of time for exhaustion (i.e., the migration of the dye molecules from solution to the substrate surface). Electrolytes are added to the solution to salt out the dye molecules during exhaustion so they will associate with or be fixed on to the substrate. The substrate is then removed from the dye solution and the excess unfixed dye is rinsed off in a multi-step process using large quantities of water.

Commercially available dyes are generally hydrophobic and, therefore, require large quantities of water for excess dye to be rinsed off from the substrate after application. The present methods reduce both water and salt waste streams and, therefore, can lower overall process costs and reduce or eliminate significant regulatory burden. Using the present methods as described above, a hydrophobic substituent can be linked to various dyes. Cleavage or activation of this substituent, by applying a stimulus, changes the dye molecule from more hydrophobic to less hydrophobic (or more hydrophilic). The hydrophobicity is changed after fixation of the dye on the substrate, and the unfixed dye molecules can be removed in a single rinsing step. Different dye moiety-hydrophobic moiety conjugates respond to different types of stimulus. Illustrations of systems that work according to this concept are given in the Examples section below.

Using thermal stimulus: Several hydrophobic esters are known to thermally decompose, several at temperatures less than 140° C. An example showing thermal decomposition of a polymer in order to change its solubility properties is shown below. The hydrophobic chain removed from the polymer through thermolysis is volatile and will evaporate from the wastewater and can be captured in a conventional air scrubber.

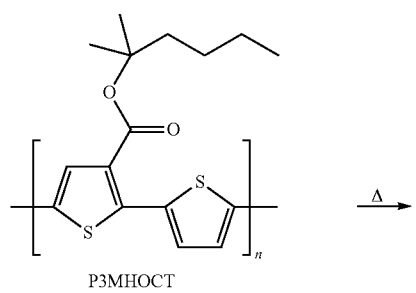

P3MHOCT

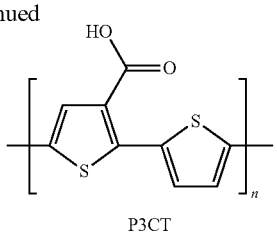

P3CT

Thermal decomposition of the soluble polythiophene (P3 MHOCT) liberates the highly volatile 2-methylhexene, which evaporates from the bath into an air scrubber. This strategy may be adapted to any dye having a carboxylic acid group. Dyes with carboxylic acid groups such as, but not limited to, C.I. Reactive Red 221 are commercially available and other dyes can be functionalized to work with this chemistry.

A method for a dying process using a thermal stimulus includes: applying reactive dye with the hydrophobic ester substituent to the substrate, typically by soaking the substrate in aqueous dye solution; waiting for exhaustion (i.e., the migration of the dye molecules from solution to the substrate surface), and raising the system pH to about 12 to fix the dye to the substrate. The substrate may then be removed from the solution and heated to remove the water. The substrate may be heated further to about 140° C. for about 20 minutes to about 60 minutes to remove the thermolysis product (which may be carried off as a gas). The substrate is then rinsed to remove excess hydrophilic dye. These temperatures, times, and pH values are merely examples, and may be readily changed by a skilled artisan.

Using photo stimulus: Photo-deprotection or photolysis of hydrophobic moieties is typically conducted in the 400 nm range using UV light. In this wavelength range, many commercially available dyes have low absorptivities and, accordingly, the dye will not impact the photolysis of the hydrophobic moiety. Many photolabile groups which can be cleaved at around 400 nm are known in the art. The majority of currently used photolabile linkers are based on the nitrobenzyl group, as shown below. There are also photolabile groups based on Coumarin, such as coumarin-4-yl-methoxy carbonates, which when photolyzed give $CO_2$ and an alcohol (which could be hydrophobic). Such groups are described in, e.g., Suzuki et. al., *Organic letters*. 2003 December 11; 5(25): 4867-70. A prototypical example is the 2-nitrobenzyl group which can be cleaved in this wavelength range to reveal alcohols as shown in Scheme IV below:

Scheme IV

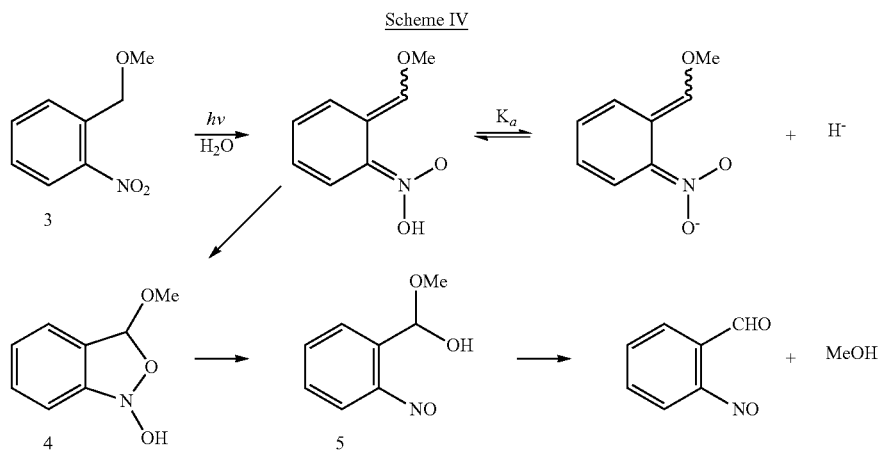

For example, if the 2-nitrobenzyl molecule in Scheme IV is attached to a dye moiety and photolyzed after application of the dye to the substrate, it would result in a hydrophilic alcohol dye as shown in scheme V:

Scheme V

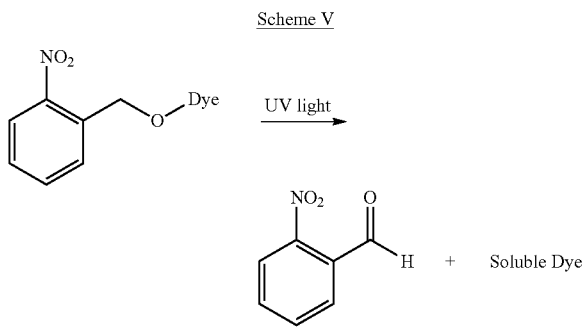

A method for a dying process using photo stimulus includes: applying reactive dye having the nitrobenzyl substituent to the substrate, waiting for exhaustion, and raising the system pH to fix the dye to the substrate. The substrate may then be exposed to a photo stimulus, such as light, to cleave the dye molecule into hydrophilic fragments. In some embodiments, the light source is a UV light source. In some embodiments, the light source is a Xenon-Mercury short arc lamp. In various embodiments, the substrate is exposed to the photo stimulus for at least about 10 minutes, at least about 20 minutes or at least about 30 minutes. Finally, the hydrophilic fragments may be rinsed off using lesser quantities of water. This photolabile substituent, light, source, and times are merely examples, and may be readily changed by a skilled artisan.

Using enzyme as stimulus: In this approach, the dye moiety can be attached to a fatty acid chain. This is achieved by esterifying a suitable dye having an alcohol group with a suitable fatty acid. The dye-fat conjugate can then be hydrolyzed using a lipase-type or amylase-type enzyme, to liberate the free fatty acid along with a more hydrophilic alcohol dye moiety as shown in Scheme VI. Suitable enzymes include commercially available enzymes such as, but not limited to, SEBright LP® or enzymes described in U.S. Pat. No. 6,306, 813. For the hydrolysis reaction, parameters such as pH, time and concentration of the enzyme can be optimized by standard methods known in the art, depending on the type of enzyme used. Suitable pH includes, for example, basic pH in the range of about 8 to about 12. An enzyme concentration of about 1 μg/ml can be used. In some embodiments, the hydrolysis reaction can be conducted at a temperature of about 25° C. to about 85° C. In other embodiments, the temperature of the hydrolysis reaction is about 45° C. to about 65° C.

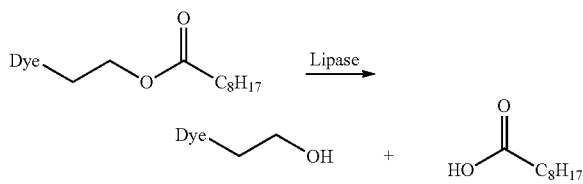

The total volume of water needed for rising off excess dye is dramatically reduced by this approach. Further, application of more hydrophobic dye molecules enables a higher fixation rate which reduces the total amount of unfixed dye to be rinsed off.

A method for a dying process using enzyme stimulus includes: applying a reactive dye having a fat substituent to the substrate, waiting for exhaustion, and raising the system pH to fix the dye to the substrate. The substrate may then be exposed to an enzyme, such as a lipase, to cleave the dye molecule into a fatty acid and a hydrophilic dye. Finally, the substrate is rinsed to remove the excess hydrophilic dye. Other enzymatically cleavable substituents may be used with an appropriate enzyme. Exemplary combinations include, a nucleoside and a nuclease enzyme or an amide group and a protease enzyme, such as a subtilisin (e.g., Subtilisin 309), which is well-known to have great substrate generality and can function at higher pHs.

In one embodiment, the dye compound includes a hydrophilic dye moiety; and a hydrophobic moiety bonded to the hydrophilic dye moiety through a linker moiety; wherein the linker moiety is cleaved in response to a stimulus; and the dye compound is represented by Formula (I)

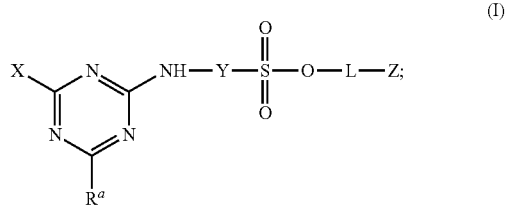

wherein Z is the hydrophobic moiety; L is the linker moiety; Y is a phenyl or a naphthyl group; X is H, Cl, Br, F, or I; $R^a$ is a halogen, or —$NR^b$—W group; $R^b$ is H or an alkyl group; and W comprises a phenyl, naphthyl or anthracenyl group.

In one embodiment, the dye compound includes a hydrophilic dye moiety; and a hydrophobic moiety bonded to the hydrophilic dye moiety through a linker moiety; wherein the linker moiety is cleaved in response to a stimulus; and the dye compound is represented by Formula (II)

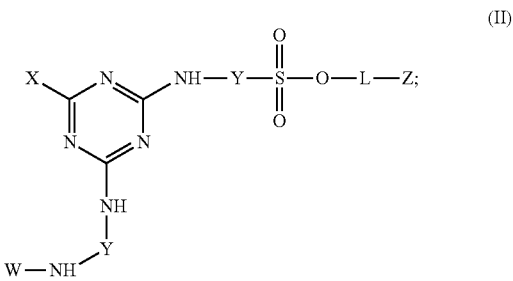

wherein Z is the hydrophobic moiety; L is the linker moiety; X is H, Cl, Br, F, or I; each Y independently comprises a phenyl or a naphthyl group; and W comprises a phenyl, naphthyl or anthracenyl group.

In one embodiment, the dye compound includes a hydrophilic dye moiety; and a hydrophobic moiety bonded to the hydrophilic dye moiety through a linker moiety; wherein the linker moiety is cleaved in response to a stimulus; and the dye compound is represented by Formula (III)

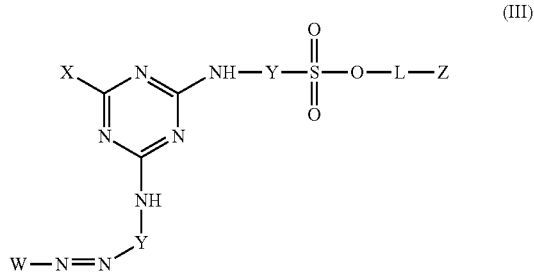

wherein Z is the hydrophobic moiety; L is the linker moiety; X is H, Cl, Br, F, or I; each Y independently comprises a phenyl or a naphthyl group; and W comprises a phenyl, naphthyl, anthracenyl or pyrazolinyl group.

In one embodiment, the dye compound includes a hydrophilic dye moiety; and a hydrophobic moiety bonded to the hydrophilic dye moiety through a linker moiety; wherein the linker moiety is cleaved in response to a stimulus; and the dye compound is represented by Formula (IV)

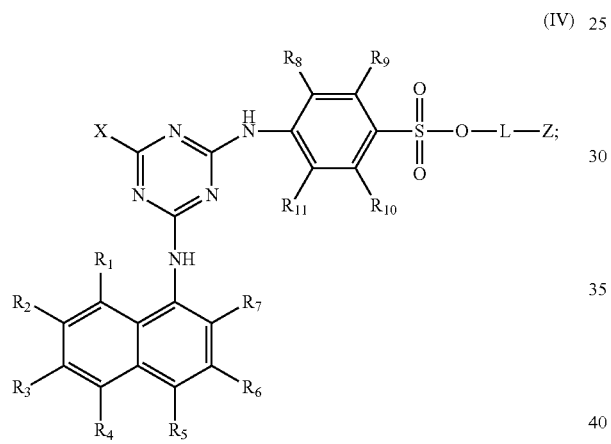

wherein Z is the hydrophobic moiety; L is the linker moiety; X is H, Cl, Br, F, or I; $R_1$, $R_2$, $R_3$, $R_4$, $R_5$, $R_6$, and $R_7$ may be the same or different and are independently H, Cl, Br, F, I, —$NO_2$, —OH, alkyl, aryl, or —$S(=O)_3R_{12}$; $R_8$, $R_9$, $R_{10}$, and $R_{11}$ may be the same or different and are independently H or alkyl; and $R_{12}$ is H or an alkali metal.

In some embodiments, Z is an alkyl group, a cycloalkyl group, or an aryl group.

In some embodiments, the L is a direct bond, an ester, ether, amide, carbonyl, phosphate, sulfoxide, nitrophenyl, nitrobenzyl, alkoxybenzoin, phenacyl, or benzylthioether group.

In one embodiment, a method for modulating the solubility of a dye compound is provided, wherein the method includes exposing a dye composition to a stimulus; and contacting a substrate and the dye composition for a time period sufficient to covalently bond at least a portion of the plurality of the dye compounds to the substrate, prior to exposing the dye composition to the stimulus. In some embodiments, the dye composition includes a plurality of the dye compounds, and each dye compound includes a hydrophilic dye moiety; and a hydrophobic moiety bonded to the hydrophilic dye moiety through a linker moiety; and the linker moiety is cleaved in response to the stimulus.

In some embodiments, the method further includes washing the substrate with water to remove the hydrophilic dye moiety after exposing the dye composition to the stimulus. In some embodiments, the substrate is selected from the group consisting of fabric, paper, plastics, glass, metals, wood, hair, fur, oils, waxes, leather and food. In an illustrative embodiment, the substrate is a fabric.

The present technology offers a flexible approach to improving fixing efficiency and reducing water use simultaneously, without interfering with either the coloring or fixing properties of the dye. The present methods have several advantages such as high rate of fixation of dyes, low quantities of electrolyte in the application bath, ease of rinsing off excess dye and overall reduction in water and dye usage.

The present technology, thus generally described, will be understood more readily by reference to the following examples which are provided by way of illustration and are not intended to be limiting in any way.

EXAMPLES

The present technology is further illustrated by the following examples which should not be construed as limiting in any way.

Example 1A

Preparation of Dye Compound

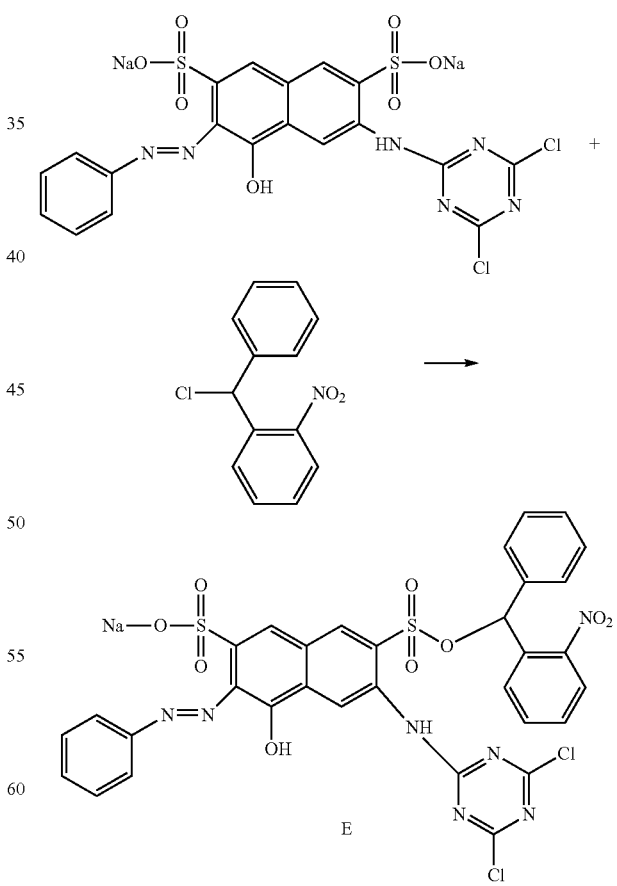

The sulfonate group of Procion Red MX-5B is made to react with the halo group in the photolabile compound such as 1-(chloro(phenyl)methyl)-2-nitrobenzene and forms a hydrophobic conjugate E which is then applied to the substrate.

Example 1B

Removal of Photolabile Group by Photolysis

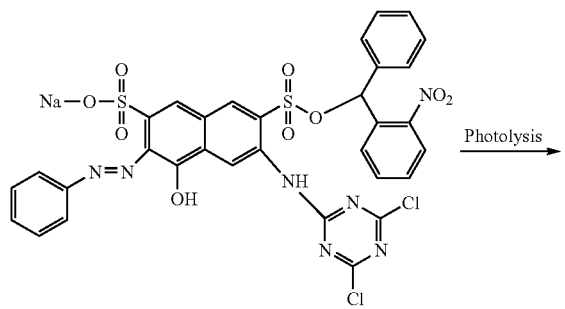

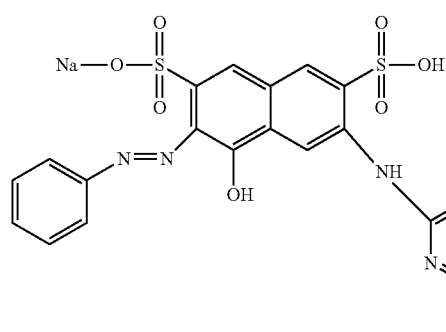

Once the application process is complete, the dye solution is photolyzed to remove the photolabile group thereby recreating the hydrophilic dye moiety, which is easily washed away using decreased quantities of water.

Example 2A

Preparation of Dye Compound

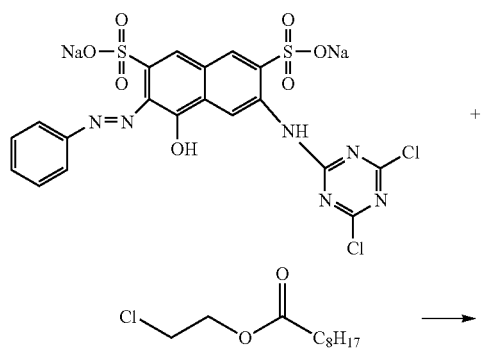

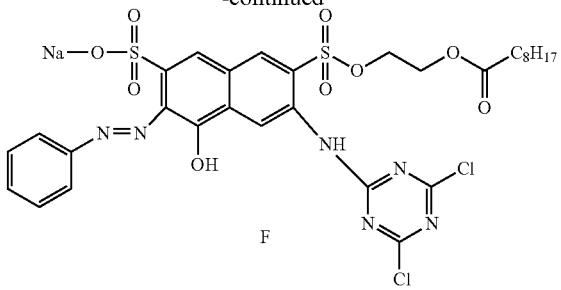

The sulfonate group of Procion Red MX-5B is reacted with a fatty acid chloride, such as 2-chloroethyl nonanoate to obtain the dye-fat conjugate F.

Example 2B

Removal of Using an Enzyme

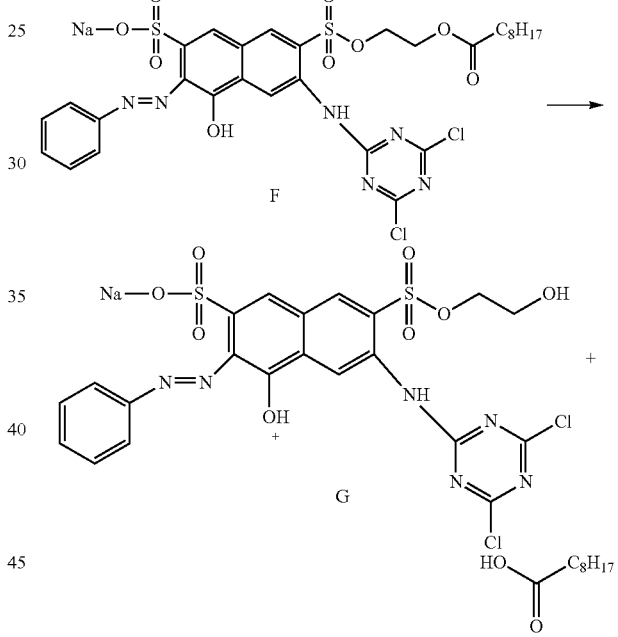

The dye-fat conjugate F is then applied to a substrate, such as fabric. The excess unattached dye is hydrolyzed using a SEBright LP® enzyme, to liberate the free fatty acid along with the hydrophilic alcohol dye moiety G. The excess hydrophilic dye is washed off using decreased quantities of water.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

The embodiments, illustratively described herein, may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, includes the number recited and refers to ranges which can be subsequently broken down into subranges as discussed above. Finally, as will be understood by one skilled in the art, a range includes each individual member.

Other embodiments are set forth in the following claims.

What is claimed is:

1. A dye compound comprising:

a hydrophilic dye moiety; and a hydrophobic moiety bonded to the hydrophilic dye moiety through a linker moiety;

wherein:

the linker moiety is cleaved in response to a stimulus;

the dye compound is represented by Formula (I)

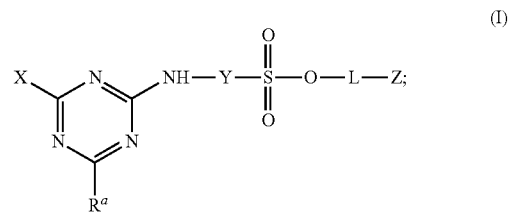

Z is the hydrophobic moiety;

L is the linker moiety;

Y is a phenyl or a naphthyl group;

X is H, Cl, Br, F, or I;

$R^a$ is a halogen, or —$NR^b$—W group;

$R^b$ is H or an alkyl group; and

W comprises a phenyl, naphthyl or anthracenyl group.

2. A dye compound comprising:

a hydrophilic dye moiety; and a hydrophobic moiety bonded to the hydrophilic dye moiety through a linker moiety;

wherein:

the linker moiety is cleaved in response to a stimulus; the dye compound is represented by Formula (II)

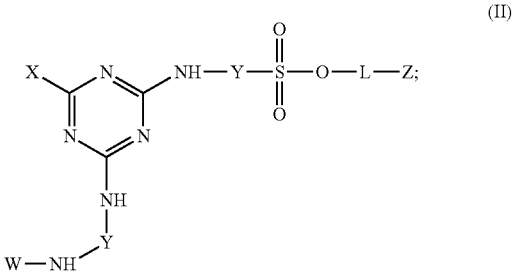

Z is the hydrophobic moiety;

L is the linker moiety;

X is H, Cl, Br, F, or I;

each Y independently comprises a phenyl or a naphthyl group; and

W comprises a phenyl, naphthyl or anthracenyl group.

3. A dye compound comprising:

a hydrophilic dye moiety; and a hydrophobic moiety bonded to the hydrophilic dye moiety through a linker moiety;

wherein:
the linker moiety is cleaved in response to a stimulus; the dye compound is represented by Formula (III)

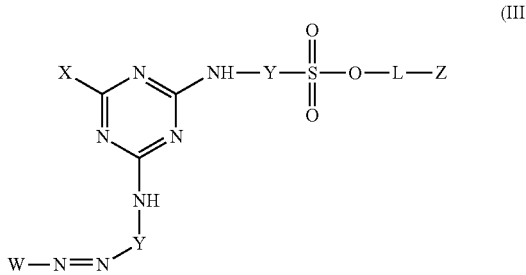

Z is the hydrophobic moiety;
L is the linker moiety;
X is H, Cl, Br, F, or I;
each Y independently comprises a phenyl or a naphthyl group; and
W comprises a phenyl, naphthyl, anthracenyl or pyrazolinyl group.

4. A dye compound comprising:
a hydrophilic dye moiety; and
a hydrophobic moiety bonded to the hydrophilic dye moiety through a linker moiety;
wherein:
the linker moiety is cleaved in response to a stimulus; the dye compound is represented by Formula (IV)

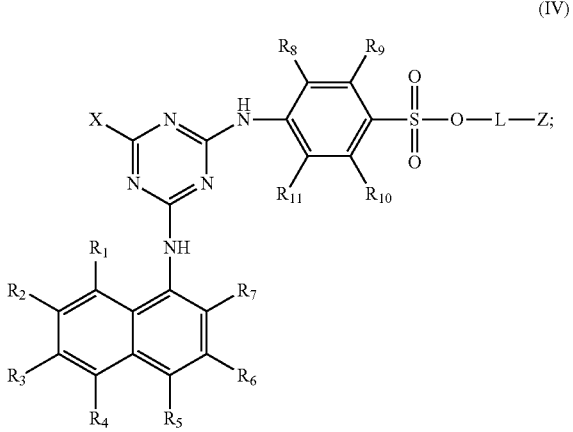

Z is the hydrophobic moiety;
L is the linker moiety;
X is H, Cl, Br, F, or I;

$R_1$, $R_2$, $R_3$, $R_4$, $R_5$, $R_6$, and $R_7$ may be the same or different and are independently H, Cl, Br, F, I, $-NO_2$, $-OH$, alkyl, aryl, or $-S(=O)_3R_{12}$;
$R_8$, $R_9$, $R_{10}$, and $R_{11}$ may be the same or different and are independently H or alkyl; and
$R_{12}$ is H or an alkali metal.

5. The dye compound of claim 1, wherein Z is an alkyl group, a cycloalkyl group, or an aryl group.

6. The dye compound of claim 1, wherein L is a direct bond, an ester, ether, amide, carbonyl, phosphate, sulfoxide, nitrophenyl, nitrobenzyl, alkoxybenzoin, phenacyl, or benzylthioether group.

7. A method for modulating the solubility of a dye compound comprising:
exposing a dye composition to a stimulus; and
contacting a substrate and the dye composition for a time period sufficient to covalently bond at least a portion of the plurality of the dye compounds to the substrate, prior to exposing the dye composition to the stimulus;
wherein:
the dye composition comprises:
a plurality of the dye compounds, each dye compound comprising:
a hydrophilic dye moiety; and
a hydrophobic moiety bonded to the hydrophilic dye moiety through a linker moiety; and
the linker moiety is cleaved in response to the stimulus.

8. The method of claim 7, further comprising washing the substrate with water to remove the hydrophilic dye moiety after exposing the dye composition to the stimulus.

9. The method of claim 7, wherein the substrate is selected from the group consisting of fabric, paper, plastics, glass, metals, wood, hair, fur, oils, waxes, leather and food.

10. The method of claim 7, wherein the substrate is a fabric.

11. The dye compound of claim 2, wherein Z is an alkyl group, a cycloalkyl group, or an aryl group.

12. The dye compound of claim 3, wherein Z is an alkyl group, a cycloalkyl group, or an aryl group.

13. The dye compound of claim 4, wherein Z is an alkyl group, a cycloalkyl group, or an aryl group.

14. The dye compound of claim 2, wherein L is a direct bond, an ester, ether, amide, carbonyl, phosphate, sulfoxide, nitrophenyl, nitrobenzyl, alkoxybenzoin, phenacyl, or benzylthioether group.

15. The dye compound of claim 3, wherein L is a direct bond, an ester, ether, amide, carbonyl, phosphate, sulfoxide, nitrophenyl, nitrobenzyl, alkoxybenzoin, phenacyl, or benzylthioether group.

16. The dye compound of claim 4, wherein L is a direct bond, an ester, ether, amide, carbonyl, phosphate, sulfoxide, nitrophenyl, nitrobenzyl, alkoxybenzoin, phenacyl, or benzylthioether group.

* * * * *

UNITED STATES PATENT AND TRADEMARK OFFICE
CERTIFICATE OF CORRECTION

PATENT NO. : 8,246,698 B2 Page 1 of 1
APPLICATION NO. : 13/126132
DATED : August 21, 2012
INVENTOR(S) : Miller It is certified that error appears in the above-identified patent and that said Letters Patent is hereby corrected as shown below:

In Column 14, in Table 1, Line 6, delete

" 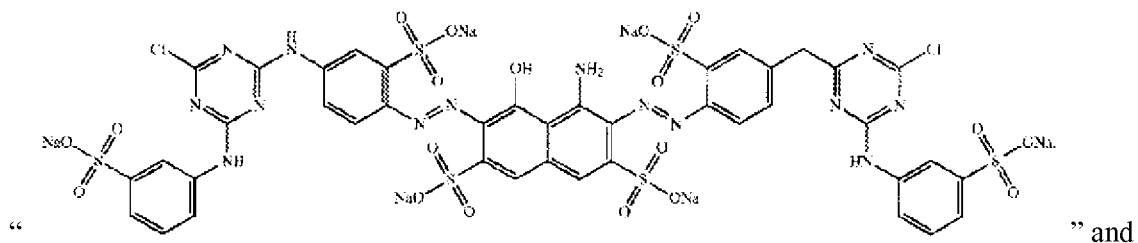 " and insert -- 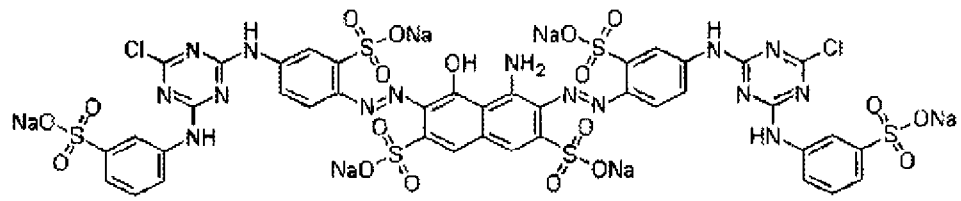 --, therefor.

In Column 19, Line 32, delete "light," and insert -- light --, therefor.

Signed and Sealed this
Twenty-third Day of October, 2012

David J. Kappos
*Director of the United States Patent and Trademark Office*